US006063902A

United States Patent [19]
Stiegler

[11] Patent Number: 6,063,902
[45] Date of Patent: May 16, 2000

[54] ECTOPARASITE HISTAMINE RELEASING FACTOR, GENES AND USES THEREOF

[75] Inventor: Gary L. Stiegler, Ft. Collins, Colo.

[73] Assignee: Heska Corporation, Ft. Collins, Colo.

[21] Appl. No.: 09/004,053

[22] Filed: Jan. 7, 1998

Related U.S. Application Data

[62] Division of application No. 08/690,849, Aug. 1, 1996, Pat. No. 5,952,194.

[51] Int. Cl.[7] .............................. C07K 1/00; C07K 16/00; A61K 39/00; A61K 14/00; A61K 38/00
[52] U.S. Cl. ................... 530/350; 424/184.1; 424/185.1; 424/191.1; 424/265.1; 424/278.1; 424/275.1; 424/276.1; 530/300; 530/324; 530/325; 530/326; 530/327; 530/328; 530/329; 530/361; 530/858; 435/69.1; 435/69.3
[58] Field of Search .............................. 424/184.1, 185.1, 424/191.1, 265.1, 275.1, 278.1, 276.1; 530/350, 858; 435/69.1, 69.3, 300, 324, 325, 326, 327, 328, 329, 361

[56] References Cited

U.S. PATENT DOCUMENTS

| 4,879,213 | 11/1989 | Fox et al. ...................................... 435/5 |
| 4,939,039 | 7/1990 | McGrogan et al. . |
| 5,356,622 | 10/1994 | Heath et al. .......................... 424/265.1 |
| 5,952,194 | 9/1999 | Steigler . |

FOREIGN PATENT DOCUMENTS

| WO 92/13889 | 8/1992 | WIPO . |
| WO 92/13890 | 8/1992 | WIPO . |
| 9412881 | 6/1994 | WIPO . |
| WO 96/140089 | 5/1996 | WIPO . |

OTHER PUBLICATIONS

Burgess, et al., 1990, *J. of Cell Biology*, 111:2129–2138.
Lazar et al., 1988, *Molecular and Cellular Biology*, 8(3):1247–1252.
Liao, et al., *J. Allergy Clin. Immunol.*, 86(6)(Part 1):894–901, Dec. 1990.
MacDonald, et al., *Science*, 269:688–690, Aug. 1995.
Matuszek, et al., *Natural Toxins*, 36–43, 1994.
Toki, et al., *Biomed. Res.*, 9(1):75–79, 1988.
Toki, et al., *Biomed. Res.*, 9(6):421–428, 1988.
Wanstall, et al., *Toxicon*, 12:649–655, 1974.
Gross, et al. *NAR*, 17(20):83679 (1989).

*Primary Examiner*—Nita Minnifield
*Attorney, Agent, or Firm*—Sheridan Ross P.C.

[57] ABSTRACT

The present invention relates to ectoparasite histamine releasing factor (HRF) proteins; to ectoparasite HRF nucleic acid molecules, including those that encode such HRF proteins; to antibodies raised against such HRF proteins; and to compounds that inhibit ectoparasite HRF activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to reduce ectoparasite burden of animals.

14 Claims, No Drawings

ECTOPARASITE HISTAMINE RELEASING FACTOR, GENES AND USES THEREOF

CROSS REFERENCE TO RELATED APPLICATIONS

This application is a divisional of U.S. application Ser. No. 08/690,849, filed Aug. 1, 1996, entitled "ECTOPARASITE HISTAMINE RELEASING FACTOR, GENES AND USES THEREOF" now U.S. Pat. No. 5,952,194.

FIELD OF THE INVENTION

The present invention relates to novel ectoparasite histamine releasing factor (HRF) nucleic acid molecules, to proteins encoded by such nucleic acid molecules, to antibodies raised against such proteins, and to inhibitors of such proteins, as well as to the use of such compositions to reduce ectoparasite infestation.

BACKGROUND OF THE INVENTION

Ectoparasite infestation of animals is of health and economic concern because ectoparasites are known to cause and/or transmit a variety of diseases. Ectoparasites cause and/or carry infectious agents that cause, for example, allergy dermatitis, anemia, murine typhus, plague and tapeworm. In addition, ectoparasites, in particular fleas, are a problem for animals maintained as pets because the infestation becomes a source of annoyance for the pet owner who may find his or her home generally contaminated with ectoparasites which feed on the pets. As such, ectoparasites are a problem not only when they are on an animal but also when they are in the general environment of the animal.

In addition, ectoparasite bites, such as flea bites, can cause a hypersensitive response in animals. For example, hypersensitive responses to flea bites is manifested in a disease called flea allergy dermatitis (FAD). Hypersensitivity refers to a state of altered reactivity in which an animal, having been previously exposed to a compound, exhibits an allergic response to the compound upon subsequent exposures. There are four major types of hypersensitive responses (described in detail in, for example, Janeway et al., in *Immunobiology*, Garland Publishers, N.Y., N.Y., 1994). FAD can have manifestations of both immediate and delayed-type hypersensitivity. Typically, an immediate hypersensitive response in an animal susceptible to FAD includes wheal formation at the site of a bite. Such wheals can develop into a papule with a crust, representative of delayed-type hypersensitivity.

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

The medical and veterinary importance of ectoparasite infestation has prompted the development of reagents capable of controlling ectoparasite infestation. Commonly encountered methods to control ectoparasite infestation are generally focussed on use of insecticides in formulations such as sprays, shampoos, dusts, dips, or foams, or in pet collars. While some of these products are efficacious, most, at best, offer protection of a very limited duration. Furthermore, many of the methods are often not successful in reducing ectoparasite populations on the pet for one or more of the following reasons: (1) failure of owner compliance (frequent administration is required); (2) behavioral or physiological intolerance of the pet to the pesticide product or means of administration; and (3) the emergence of ectoparasite populations resistant to the prescribed dose of pesticide. Additional anti-ectoparasite products include chemical drugs that can, for example, affect the development of ectoparasitic larvae.

Prior investigators have determined that histamine can be released in mammals in response to ectoparasite bites. A variety of biological mechanisms can be responsible for the release of histamine in an animal. only mammalian histamine releasing factors, however, have been defined; see, for example, Wanstall et al., *Toxicon* 12:649–655, 1974; Toki et al., *Biomedical Research* 9(1):75–79, 1988; Toki et al., *Biomedical Research* 9(1):421–428, 1988; Liao et al., *J. Allergy Clin. Immunol.* 86:894–901, 1990; and Matuszek et al., *Natural Toxins* 2:36–43, 1994.

Thus, there remains a need to identify an efficacious compound capable of reducing ectoparasite burden on animals, desensitizing animals to ectoparasite allergens and/or reducing inflammation in an animal.

SUMMARY OF THE INVENTION

The present invention relates to a novel product and process for reducing ectoparasite infestation, desensitizing animals to ectoparasite allergens and/or reducing inflammation in an animal. The present inventors have made the surprising discovery that an ectoparasite produces a histamine releasing factor-like protein. Such a protein can be a target for vaccines and anti-inflammatory reagents useful to prevent or treat, for example, allergy dermatitis in an animal.

The present invention includes ectoparasite histamine releasing factor (HRF) proteins; ectoparasite HRF nucleic acid molecules, including those that encode such proteins; antibodies raised against such HRF proteins (i.e., anti-ectoparasite HRF antibodies); and other compounds that inhibit ectoparasite HRF activity (i.e, inhibitory compounds or inhibitors). Also included are methods to obtain and use such proteins, nucleic acid molecules, antibodies and inhibitory compounds.

One embodiment of the present invention is an isolated ectoparasite nucleic acid molecule that hybridizes under stringent hybridization conditions with a flea histamine releasing factor gene (i.e., a flea HRF gene, such a nucleic acid molecule is referred to as an ectoparasite HRF nucleic acid molecule). A flea HRF gene preferably includes nucleic acid sequences SEQ ID NO:1 and SEQ ID NO:3. The present invention also relates to recombinant molecules, recombinant viruses and recombinant cells that include one or more HRF nucleic acid molecules of the present invention. Also included are methods to produce such nucleic acid molecules, recombinant molecules, recombinant viruses and recombinant cells.

Another embodiment of the present invention includes an isolated ectoparasite histamine releasing factor protein (i.e., an ectoparasite HRF protein). A preferred ectoparasite HRF protein comprises amino acid sequence SEQ ID NO:2. The present invention also relates to mimetopes of ectoparasite HRF proteins as well as to isolated antibodies that selectively bind to ectoparasite HRF proteins or mimetopes thereof). Also included are methods, including recombinant methods, to produce proteins, mimetopes and antibodies of the present invention.

Yet another embodiment of the present invention is a therapeutic composition that is capable of reducing ectoparasite burden of an animal. Such a therapeutic composition includes one or more of the following compounds: an isolated HRF protein encoded by a nucleic acid molecule that hybridizes under stringent hybridization conditions with a flea HRF gene, or a mimetope of such protein; an isolated nucleic acid molecule that hybridizes under stringent hybridization conditions with a flea HRF gene; an isolated antibody that selectively binds to an ectoparasite HRF protein; and/or an inhibitor of ectoparasite HRF activity identified by its ability to inhibit flea HRF activity (including HRF ligands and analogs).

Another embodiment of the present invention is a therapeutic composition that is capable of reducing inflammation in an animal. Such a therapeutic composition includes one or more of the following compounds: an isolated ectoparasite HRF protein or a mimetope thereof; an isolated ectoparasite nucleic acid molecule that hybridizes under stringent hybridization conditions with a flea HRF gene; an isolated antibody that selectively binds to an ectoparasite HRF protein; a peptide derived from such an antibody; and/or an inhibitor of ectoparasite HRF activity identified by its ability to inhibit flea HRF activity (including HRF ligands and analogs, and mixtures thereof. Also included in the present invention is a method to reduce ectoparasite burden in an animal, comprising the step of administering to the animal a therapeutic composition of the present invention.

The present invention also includes the use of HRF proteins of the present invention to identify or obtain ectoparasite HRF receptors, as well as in assays for diagnosing and prescribing treatment of allergic dermatitis.

DETAILED DESCRIPTION OF THE INVENTION

The present invention provides ectoparasite histamine releasing factor (HRF) proteins and nucleic acid molecules, antibodies directed against ectoparasite HRF proteins and other inhibitors of ectoparasite HRF activity. Also included in the present invention is the use of these proteins, nucleic acid molecules, antibodies and other inhibitors, as well as therapeutic compositions, to reduce ectoparasite burden of an animals as well as in other applications (e.g., allergic inflammation), such as those disclosed below. The invention is particularly advantageous in that it provides for unique compounds useful as a target for a vaccine and to develop compounds that protect (i.e., treat or prevent) an animal from allergy dermatitis. The discovery that ectoparasites express an HRF is surprising in that until now only mammalian HRF's have been identified. Particularly surprising is that flea HRF proteins of the present invention have n-terminal amino acid sequence similar to the human n-terminal amino acid sequence of human HRF that has also been identified as a tumor factor (MacDonald et al., Science, vol. 269, pp. 688690, 1995). This discovery led to the identification of the novel ectoparasite histamine releasing compounds of the present invention.

One embodiment of the present invention is an isolated protein comprising an ectoparasite HRF protein. It is to be noted that the term "a" or "an" entity refers to one or more of that entity; for example, a protein refers to one or more proteins, or to at least one protein. As such, the terms "aa" (or "an"), "one or more" and "at least one" can be used interchangeably herein. It is also to be noted that the terms "comprising", "including", and "having" can be used interchangeably. An isolated ectoparasite HRF protein can, for example, be obtained from its natural source, be produced using recombinant DNA technology, or be synthesized chemically. As used herein, an isolated ectoparasite protein can be a full-length ectoparasite HRF protein or any homologue of such a protein, such as an ectoparasite HRF protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A homologue of an ectoparasite HRF protein is a protein having an amino acid sequence that is sufficiently similar to a natural ectoparasite HRF protein amino acid sequence that a nucleic acid sequence encoding the homologue is capable of hybridizing under stringent conditions to (i.e., with) a nucleic acid molecule encoding the natural ectoparasite HRF protein (i.e., to the complement of the nucleic acid strand encoding the natural ectoparasite HRF protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual,* Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite HRF protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite HRF protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite HRF protein homologues can be the result of natural allelic variation or natural mutation. HRF protein homologues of the present invention can also be produced using techniques known in the art including, but not limited to, direct modifications to the protein or modifications to the gene encoding the protein using, for example, classic or recombinant DNA techniques to effect random or targeted mutagenesis.

A homologue of an ectoparasite HRF protein of the present invention also includes a homologue that, when the homologue is administered to an animal as an immunogen, using techniques known to those skilled in the art, the animal will produce an immune response against at least one epitope of a natural ectoparasite HRF protein. The ability of a protein to effect an immune response, can be measured using techniques known to those skilled in the art. HRF protein homologues of the present invention also include HRF proteins that selectively bind to antisera that selectively binds to flea saliva proteins. Methods to produce and use antiserum are disclosed, for example, in PCT Publication No. WO 96/11271, entitled "NOVEL ECTOPARASITE SALIVA PROTEINS AND APPARATUS TO COLLECT SUCH PROTEINS", published Apr. 18, 1996, application Ser. No. PCT/US95/13,200; which is incorporated herein by this reference in its entirety).

Isolated HRF proteins of the present invention, including full-length proteins as well as homologues, can be identified in a straight-forward manner by the proteins ability to elicit an immune response against natural ectoparasite HRF proteins, to mediate histamine release and/or to selectively bind to antiserum that binds specifically to flea saliva proteins.

Isolated HRF proteins of the present invention have the further characteristic of being encoded by nucleic acid molecules that hybridize under stringent hybridization conditions to a gene encoding a flea HRF protein. As used herein, a flea HRF gene includes all nucleic acid sequences related to a flea HRF gene such as regulatory regions that control production of the flea HRF protein encoded by that gene (such as, but not limited to, transcription, translation or post-translation control regions) as well as the coding region itself. In one embodiment, a flea HRF gene of the present invention includes the nucleic acid sequence SEQ ID NO:1 as well as the complement of SEQ ID NO:1. Nucleic acid sequence SEQ ID NO:1 represents the deduced sequence of the coding strand of a cDNA (complementary DNA) nucleic acid molecule denoted herein as nfHRF$_{693}$ (wherein "f" denotes Ctenocephalides felis), the production of which is disclosed in the Examples. The complement of SEQ ID NO:1 which refers to the nucleic acid sequence of the strand complementary to the strand having SEQ ID NO:1 and can easily be determined by those skilled in the art, is represented herein as SEQ ID NO:3. It should be noted that since nucleic acid sequencing technology is not entirely error-free, SEQ ID NO:1 and other nucleic acid and protein sequences presented herein, at best, represent apparent sequences of HRF nucleic acid molecules and HRF proteins of the present invention.

In another embodiment, a flea HRF gene can be an allelic variant that includes a similar but not identical sequence to SEQ ID NO:1. An allelic variant of a flea HRF gene including SEQ ID NO:1, is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art and would be expected to be found within a given ectoparasite since the genome is diploid and/or among a group of two or more ectoparasites.

Suitable ectoparasites from which to isolate HRF proteins of the present invention (including isolation of the natural protein or production of the protein by recombinant or synthetic techniques) include biting gnat, bee, wasp, ant, flea, fly, mosquito, tick, mite, lice, spider, ant and true bug. Preferred fleas from which to isolate HRF proteins include fleas of the genus Ctenocephalides, Ceratophyllus, Diamanus, Echidnophaga, Nosopsyllus, Pulex, Tunga, Xenopsylla, Oropsylla or Orchopeus. Particularly preferred fleas are those of the species Ctenocephalides felis, Ctenocephalides canis, Pulex irritans, Pulex simulans, Ceratophyllus pulicidae, Oropsylla (Thrassis)bacchi, Oropsylla (Diamanus) Montana, Orchopeus howardi, Xenopsylla cheopis.

The present invention also includes mimetopes of HRF proteins of the present invention. As used herein, a mimetope of a HRF protein of the present invention refers to any compound that is able to mimic the activity of such a HRF protein, often because the mimetope has a structure that mimics the HRF protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic or inorganic molecules, and screening such samples by affinity chromatography techniques using the corresponding binding partner.

One embodiment of the present invention is a fusion protein that includes an ectoparasite HRF protein-containing domain attached to one or more fusion segments. Suitable fusion segments for use with the present invention include, but are not limited to, segments that can: enhance a protein's stability; act as an immunopotentiator to enhance an immune response against a HRF protein; and/or assist purification of a HRF protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the HRF-containing domain of the protein and can be susceptible to cleavage in order to enable straight-forward recovery of a HRF protein. Fusion proteins are preferably produced by culturing a recombinant cell transformed with a fusion nucleic acid molecule that encodes a protein including the fusion segment attached to either the carboxyl and/or amino terminal end of a HRF-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, FL; and an S10 peptide.

In another embodiment, an ectoparasite HRF protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a HRF protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In such an embodiment, an ectoparasite HRF protein of the present invention is attached to one or more additional compounds protective against ectoparasites. In another embodiment, one or more protective compounds, such as those listed above, can be included in a multivalent vaccine comprising an ectoparasite HRF protein of the present invention and one or more of the other protective molecules as separate compounds.

A preferred isolated protein of the present invention is a protein encoded by a nucleic acid molecule that hybridizes under stringent hybridization conditions with nucleic acid molecule nfHRF$_{693}$, and particularly with nfHRF$_{501}$. A further preferred isolated protein is encoded by a nucleic acid molecule that hybridizes under stringent hybridization conditions with the complement of a nucleic acid molecule having nucleic acid sequence SEQ ID NO:1, and particularly SEQ ID NO:4. The complement of SEQ ID NO:1 is referred to herein as SEQ ID NO:3; the complement of SEQ ID NO:4 is referred to herein as SEQ ID NO:5.

Translation of SEQ ID NO:1 suggests that nucleic acid molecule nfHRF$_{693}$ encodes a partial ectoparasite HRF protein of about 167 amino acids, referred to herein as PfHRF$_{167}$, represented by SEQ ID NO:2, assuming the first codon spans from about nucleotide 1 through about nucleotide 3 of SEQ ID NO:1 and a termination (stop) codon spans from about nucleotide 502 through about nucleotide 504 of SEQ ID NO:1. The coding region encoding PfHRF$_{167}$ is represented by nucleic acid molecule nfHRF$_{501}$, having the nucleic acid sequence represented by SEQ ID NO:4 (the coding strand) and SEQ ID NO:5 (the complementary strand). The deduced amino acid sequence SEQ ID NO:2 suggests a protein having a molecular weight of about 19,307.42 kilodaltons (kD) and an estimated pI of about 4.41.

Comparison of amino acid sequence SEQ ID NO:2 (i.e., the amino acid sequence of PfHRF$_{167}$) with amino acid sequences reported in GenBank indicates that SEQ ID NO:2, showed some homology to HRF proteins of eukaryotic origin. The highest scoring match, i.e., about 53% identity, was found between SEQ ID NO:2, and mouse p21 or human p23 tumor factors, recently also identified to be HRF (MacDonald et al., ibid.).

Preferred ectoparasite HRF proteins of the present invention include proteins comprising amino acid sequences that are at least about 55%, preferably at least about 60%, and more preferably at least about 65%, and even more preferably at least about 70% identical to amino acid sequence SEQ ID NO:2. Particularly preferred are proteins comprising amino acid sequences that are at least about 75% and more particularly at least about 80% identical to amino acid sequence SEQ ID NO:2. More preferred ectoparasite HRF proteins of the present invention include: proteins encoded by at least a portion of SEQ ID NO:1 and, as such, have amino acid sequences that include at least a portion of SEQ ID NO:2. Particularly preferred HRF proteins of the present invention include SEQ ID NO:2 (including, but not limited to, SEQ ID NO:2, fusion proteins and multivalent proteins) as well as truncated homologues of proteins that comprise SEQ ID NO:2. An even more preferred protein includes PfHRF$_{167}$.

Another embodiment of the present invention is an isolated nucleic acid molecule that hybridizes under stringent hybridization conditions with a flea HRF gene. The identifying characteristics of such a gene is heretofore described. A nucleic acid molecule of the present invention can include an isolated natural ectoparasite HRF gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a flea HRF gene under stringent hybridization conditions. Suitable and preferred ectoparasites are disclosed above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated ectoparasite HRF nucleic acid molecule of the present invention can be isolated from its natural source or produced using recombinant DNA technology (e.g., polymerase chain reaction (PCR) amplification, cloning) or chemical synthesis. Isolated HRF nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a HRF protein of the present invention or to form stable hybrids under stringent conditions with natural gene isolates. An isolated HRF nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes an HRF protein of the present invention can vary due to degeneracies.

An ectoparasite HRF nucleic acid molecule homologue can be produced using a number of methods known to those skilled in the art (see, for example, Sambrook et al., ibid.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a flea HRF gene or by screening the function of a protein encoded by a nucleic acid molecule (e.g., ability to elicit an immune response against at least one epitope of a flea HRF protein, ability to selectively bind to antiserum that selectively binds to flea saliva proteins, ability to mediate histamine release).

An isolated nucleic acid molecule of the present invention can include a nucleic acid sequence that encodes at least one ectoparasite HRF protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite HRF protein.

A preferred nucleic acid molecule of the present invention, when administered to an animal, is capable of reducing ectoparasite burden of an animal. Another preferred nucleic acid molecule of the present invention, when administered to an animal, is capable of reducing inflammation in an animal, particularly inflammation caused by an ectoparasite. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal, for example, by direct injection (i.e, as a naked nucleic acid) or in a vehicle such as a recombinant virus vaccine or a recombinant cell vaccine.

One embodiment of the present invention is an ectoparasite HRF nucleic acid molecule that hybridizes under stringent hybridization conditions with nucleic acid molecule nfHRF$_{693}$ and preferably with a nucleic acid molecule having nucleic acid sequence SEQ ID NO:1 or SEQ ID NO:3. Comparison of nucleic acid sequence SEQ ID NO:1 (i.e., the nucleic acid sequence of the coding strand of nfHRF$_{693}$) with nucleic acid sequences reported in GenBank indicates that SEQ ID NO:1, showed some homology to HRF proteins of eukaryotic origin. The highest scoring match, i.e., about 60% identity, was found between SEQ ID NO:4 and human HRF.

Preferred ectoparasite HRF nucleic acid molecules include nucleic acid molecules having a nucleic acid sequence that is at least about 65%, preferably at least about 70%, more preferably at least about 75%, even more preferably at least about 80%, and even more preferably at least about 85% identical to nucleic acid sequence SEQ ID NO:4 or SEQ ID NO:5.

Another preferred nucleic acid molecule of the present invention includes at least a portion of nucleic acid sequence SEQ ID NO:1 or SEQ ID NO:3, that is capable of hybridizing to a flea HRF gene of the present invention. A more preferred nucleic acid molecule includes the nucleic acid sequence SEQ ID NO:1, SEQ ID NO:3, SEQ ID NO:4, and/or SEQ ID NO:5, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include nfHRF$_{693}$ and nfHRF$_{501}$.

The present invention also includes nucleic acid molecules encoding a protein having at least a portion of SEQ ID NO:2, including nucleic acid molecules that have been modified to accommodate codon usage properties of the cells in which such nucleic acid molecules are to be expressed.

Knowing the nucleic acid sequences of certain ectoparasite HRF nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain HRF nucleic acid molecules from other ectoparasites. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include ectoparasite cDNA libraries as well as genomic DNA libraries. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising ectoparasite HRF genes or other ectoparasite HRF nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit HRF protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of ectoparasite HRF nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (such as lambdap$_L$ and lambdap$_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, herpesvirus, vaccinia virus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with ectoparasites, such as, fleas.

Suitable and preferred nucleic acid molecules to include in recombinant vectors of the present invention are as disclosed herein. Particularly preferred nucleic acid molecule to include in recombinant vectors, and particularly in recombinant molecules, includes nfHRF$_{693}$ and nfHRF$_{501}$.

Recombinant molecules of the present invention may also (a) contain secretory signals (i.e., signal segment nucleic acid sequences) to enable an expressed ectoparasite HRF protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include ectoparasite HRF nucleic acid molecules disclosed herein. Particularly preferred nucleic acid molecules with which to transform a cell include $nfHRF_{501}$ and $nfHRF_{693}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing ectoparasite HRF proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_x3987$ and SR-11 $_x4072$; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including ectoparasite HRF nucleic acid molecules encoding one or more proteins of the present invention and one or more other proteins useful in the production of multivalent vaccines. For example, a multivalent vaccine of the present invention can include one or more nucleic acid molecules encoding one or more protective compounds in combination with an ectoparasite HRF protein of the present invention useful for reducing ectoparasite infestation, desensitizing animals to ectoparasite allergens and/or reducing inflammation in an animal.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated HRF proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce an ectoparasite HRF protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies capable of selectively binding to an ectoparasite HRF protein of the present invention or a mimetope thereof (e.g., anti-ectoparasite HRF antibodies). As used herein, the term "selectively binds to" refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-ectoparasite HRF antibody preferably selectively binds to an ectoparasite HRF protein in such a way as to reduce the activity of that protein.

Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce ectoparasite HRF proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from infestation by ectoparasites susceptible to treatment by such antibodies, (b) as reagents in assays to detect the presence, in an animal, of allergens from such ectoparasites and/or (c) as tools to screen expression libraries and/or to recover desired proteins of the present invention from a mixture of proteins and other contaminants.

One embodiment of the present invention is a formulation that can be used to diagnose and/or treat animals susceptible to or having (i.e., suffering from) allergic dermatitis. Preferred types of allergic dermatitis to diagnose and/or treat using ectoparasite HRF protein, nucleic acid molecules, antibodies and inhibitors (the collection of which is referred to herein as HRF-related products) of the present invention include flea allergy dermatitis, Culicoides allergy dermatitis, mosquito allergy dermatitis and food allergies. A preferred type of allergic dermatitis to diagnose and/or treat using ectoparasite HRF-related products of the present invention is flea allergy dermatitis. As used herein, an animal that is susceptible to allergic dermatitis refers to an animal that is genetically pre-disposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite HRF protein antibodies within an affected animal but no dermatitis). For example, sub-clinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is an in vivo test that is capable of detecting whether an animal is hypersensitive to an ectoparasite HRF protein of the present invention. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing an ectoparasite HRF protein, or a mimetope thereof. Methods to conduct skin tests of the present invention are known to those of skill in the art.

Suitable formulations to use in an in vivo skin test include ectoparasite HRF protein. A suitable amount of ectoparasite saliva product for use in a skin test of the present invention can vary widely depending on the allergenicity of the product used in the test and on the site at which the product is delivered. Suitable amounts of an ectoparasite HRF protein for use in a skin test of the present invention include an amount capable of forming reaction, such as a detectable wheal or induration (hardness) resulting from an allergic reaction to the product. Preferred amounts of an ectoparasite HRF protein in a skin test ranges from about 1 nanogram (ng) to about 500 micrograms (μg), more preferably from about 5 ng to about 300 μg, and even more preferably from about 10 ng to about 50 μg of an ectoparasite HRF protein. It is to be appreciated by those of skill in the art that such amounts will vary depending upon the allergenicity of the protein being administered.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal, such as compounds essentially incapable of inducing a hypersensitive response or simply a buffer used to prepare the formulation (e.g., saline). An example of a preferred negative control solution is phenolated phosphate buffered saline (available from Greer Laboratories, Inc., Lenoir, N.C.).

Hypersensitivity of an animal to a formulation of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes an ectoparasite HRF protein, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations.

An ectoparasite HRF protein for use with a skin test of the present invention preferably includes an ectoparasite HRF protein encoded by a nucleic acid molecule that hybridizes under stringent hybridization conditions with a flea HRF gene, more preferably includes an ectoparasite HRF protein encoded by nucleic acid SEQ ID NO:1 and/or SEQ ID NO:3 and even more preferably includes an ectoparasite HRF protein having the amino acid sequence SEQ ID NO:2.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to an ectoparasite HRF protein of the present invention by contacting a putative antibody-containing solution with a solution containing an ectoparasite HRF protein in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite HRF protein.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of immunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of an ectoparasite HRF protein of the present invention or a mimetope thereof, and of coating one or more other portions of the (or another)

solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred ectoparasite HRF proteins for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate.

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies and Fc receptors (FcR) that bind to IgE antibodies (i.e., epsilon FcR), including single chains of an FcR (e.g., the alpha chain of an epsilon FcR), as well as truncated forms with or without transmembrane domains. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

A preferred embodiment of an in vitro hypersensitivity test of the present invention comprises the steps of: (a) coating one or more portions of an ELISA plate with a suitable amount of ectoparasite HRF protein; (b) contacting the coated plate with serum, plasma or whole blood from an animal susceptible to allergic dermatitis to form immunocomplexes; and (c) contacting the immunocomplexes with an antibody that specifically binds to IgE or other compounds capable of binding to the immunocomplex, such as an epsilon Fc receptor.

Conversely, another preferred embodiment of an in vitro hypersensitivity test of the present invention comprises the steps of: (a) coating one or more portions of an ELISA plate with a suitable amount of an antibody that specifically binds to IgE or other compounds capable of binding to IgE, such as an epsilon Fc receptor; (b) contacting the coated plate with serum, plasma or whole blood from an animal susceptible to allergic dermatitis to form complexes; and (c) contacting the complexes with a suitable amount of ectoparasite HRF protein.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise an experimental sample (i.e., a formulation of the present invention) and one or more control samples bound to at least one pre-packed dipstick, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one pre-packed syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite HRF protein can be tested using an in vitro immunoabsorbent test capable of detecting IgE antibodies specific for an ectoparasite HRF protein in the animal's bodily fluid. While most animals that display delayed hypersensitivity to an ectoparasite HRF protein also display immediate hypersensitivity to the protein, a small number of animals that display delayed hypersensitivity to an allergen do not display immediate hypersensitivity to the protein. In such cases, following negative results from the IgE-specific in vitro test, the delayed hypersensitivity of the animal to an ectoparasite saliva allergen can be tested using an in vivo test of the present invention.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to an ectoparasite HRF protein and animals susceptible to hypersensitive responses against an ectoparasite HRF protein.

One embodiment of the present invention is a therapeutic composition that includes de-sensitizing compounds capable of inhibiting an immune response to an ectoparasite saliva product of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A de-sensitizing compound of the present invention can be soluble or membrane-bound. Membrane-bound de-sensitizing compounds can be associated with biomembranes, including cells, liposomes, planar membranes or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a de-sensitizing compound include, for example, at least a portion of an immunoglobulin molecule, cytokines, lectins, heterologous allergens, CD8 molecules, CD4 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the β chain of CD8. Preferred CD4 molecules include at least the extracellular functional domains of CD4. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes an HRF protein of the present invention combined with ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

Suitable therapeutic compositions of the present invention for treating flea allergy dermatitis include flea saliva extracts and other formulations including at least one flea saliva product, preferably a protein, or a mimetope thereof. Preferred therapeutic compositions include FS-1, FS-2 and/or FS-3 as well as at least a portion of at least one flea saliva product that can be isolated from FS-1, FS-2 and/or FS-3. As such, preferred formulations for use as therapeutic compositions include FS-1, FS-2, FS-3, and/or at least a portion of one or more of the proteins fspA, fspB, fspC1, fspC2, fspD1, fspD2, fspE, fspF, fspG1, fspG2, fspG3, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM (J), fspM(K), fspM(L), fspM(M), fspN(B), fspN(C), fspN (D), fspN(E), fspN(F), fspN(G), fspN(H), fspN(I), fspN(J), fspN(K), fspN(L), fspN(M), fspN(N), fspN(O) and other proteins disclosed in U.S. patent application Ser. No. 08/630,822, or homologues thereof. A more preferred flea saliva extract for use as a therapeutic compositions includes FS-1, FS-2, FS-3,and/or at least a portion of one or more of the proteins fspE, fspF, fspG1, fspG2, fspG3, fspH, fspI, fspJ1, fspJ2, fspK, fspL1, fspL2, fspM1, fspM2, fspN1, fspN2 and fspN3. A yet more preferred flea saliva extract for use as a therapeutic compositions includes FS-1, FS-2, and/or at least a portion of one or more of the proteins fspG1, fspG2, fspG3, fspH, fspM1, fspM2, fspN1, fspN2 and fspN3.

One embodiment of the present invention is a therapeutic composition that, when administered to an animal in an effective manner, is capable of reducing ectoparasite burden of that animal. As used herein, ectoparasite burden refers to reducing the potential for ectoparasite population expansion on and around an animal (i.e., reducing the ectoparasite burden). Preferably, the ectoparasite population size is decreased, optimally to an extent that the animal is no longer bothered by ectoparasites. A host animal, as used herein, is an animal from which ectoparasites can feed by attaching to and feeding through the skin of the animal. Ectoparasites can live on a host animal for an extended period of time or can attach temporarily to an animal in order to feed. At any given time, a certain percentage of an ectoparasite population can be on a host animal whereas the remainder can be in the environment surrounding the animal (i.e., in the environment of the animal). Such an environment can include not only adult ectoparasites, but also ectoparasite eggs and/or ectoparasite larvae.

Therapeutic compositions of the present invention useful for reducing ectoparasite burden include at least one of the following compounds: an isolated nucleic acid molecule that hybridizes under stringent hybridization conditions with a flea HRF gene; an isolated antibody that selectively binds to a flea HRF protein; an isolated HRF protein encoded by a nucleic acid molecule that hybridizes under stringent hybridization conditions with a flea HRF gene, or a mimetope of the protein; and/or an inhibitor of ectoparasite HRF activity identified by its ability to inhibit flea HRF activity, and a mixture thereof (i.e., combination) of at least two of the compounds. Preferred inhibitory compounds to use in a composition of the present invention include ligands and/or analogs of HRF protein. A suitable ligand includes any molecule capable of binding to an HRF protein in such a manner that the activity of the HRF protein is inhibited. Preferred ligands include, but are not limited to, antibodies and portions of antibodies, such as peptides. A suitable analog of an HRF protein includes any molecule (e.g., organic or synthetic compounds, as well as proteins) that is capable of binding to an HRF substrate in a similar manner as native HRF protein, but itself is incapable of stimulating histamine release. An inhibitor of the present invention includes non-proteinaceous compounds as well as proteinaceous compounds.

Suitable ectoparasites to target include any ectoparasite that is essentially incapable of causing allergic dermatitis and/or inflammation in an animal administered a HRF protein of the present invention. As such, a parasite to target includes any parasite that produces a protein having one or more epitopes that can be targeted by an humoral and/or cellular immune response against a HRF protein of the present invention and/or that can be targeted by a compound that otherwise inhibits HRF activity (e.g., a compound that inhibits HRF mediated histamine release), thereby resulting in the reduced ability of the ectoparasite to infest an animal. Preferred ectoparasites to target include ectoparasites disclosed herein as being useful in the production of ectoparasite proteins of the present invention. Examples of proteins, nucleic acid molecules, antibodies and inhibitors of the present invention are disclosed herein.

Another embodiment of the present invention is a therapeutic composition that, when administered to an animal in an effective manner, is capable of reducing inflammation in that animal. Inflammation refers to a protective response in an animal, generally characterized by the influx of inflammatory cells into a specific area (described in detail in Janeway et al., ibid.). Therapeutic compositions of the present invention useful for reducing inflammation include at least one of the following compounds: an isolated antibody that selectively binds to a flea HRF protein, and/or a peptide derived from that antibody, an inhibitor of ectoparasite HRF activity identified by its ability to inhibit flea HRF activity, and mixtures thereof. A therapeutic composition can also include an HRF protein, or portion thereof, that is incapable of inducing histamine release. For example, a therapeutic composition can include at least a portion of an HRF protein lacking histamine releasing activity and/or an antigenic peptide, comprising a portion of an HRF protein, that is capable of eliciting an immune response but does not induce histamine release when administered to an animal. It is within the scope of the present invention that a therapeutic composition can include a nucleic acid molecule encoding such protein or portion thereof described immediately above.

The present invention also includes a therapeutic composition comprising at least one ectoparasite HRF-based compound of the present invention in combination with at least one additional compound that either reduces ectoparasite infestation or reduces inflammation in an animal. Examples of such additional compounds include any anti-ectoparasite agent(s), including, but not limited to, proteinaceous compounds and insecticides. Preferred additional compounds are proteinaceous compounds that effect active immunization (e.g., antigen vaccines), passive immunization (e.g., antibodies), or that otherwise inhibit an ectoparasite activity that when inhibited can reduce ectoparasite burden on and around an animal. Specific examples of additional compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system; a compound that inhibits HRF activity and/or a compound that inhibits flea feeding. Examples of additional compounds useful for reducing inflammation in an animal include anti-histamines and steroids.

Therapeutic compositions of the present invention can be administered to any animal susceptible to ectoparasite infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

Therapeutic compositions of the present invention can also be administered to any ectoparasite, preferably to fleas, in such a manner that one or more components of the compositions are excreted in the feces of an ectoparasite.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor [GM-CSF], macrophage colony stimulating factor [M-CSF], granulocyte colony stimulating factor [G-CSF], colony stimulating factor [CSF], erythropoietin [EPO], interleukin-2 [IL-2], interleukin-3 [IL-3], interleukin-5 [IL- 5], interleukin-6 [IL-6], interleukin-7 [IL-7], interleukin-8 [IL-8], interleukin-10 [IL-10], interleukin-12 [IL-12], gamma interferon [IFN-y], interferon gamma inducing factor [IGIF], transforming growth factor beta, RANTES [regulated upon activation, normal T cell expressed and presumably secreted], macrophage inflammatory proteins [e.g., MIP1α and MIP1β], and Leishmania elongation initiating factor [LeIF]; bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant [Vaxcell™, Inc. Norcross, GA], Ribi adjuvants [Ribi ImmunoChem Research, Inc., Hamilton, Mont.]; and saponins and their derivatives (e.g., Quil A [Superfos Biosector A/S, Denmark]. Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, oils, other cells, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by ectoparasites. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

In order to, in an animal, reduce infestation or inflammation caused by an ectoparasite of the present invention, a therapeutic composition of the present invention is administered to the animal in an effective manner such that the composition is capable of reducing infestation or inflammation in that animal. Therapeutic compositions of the present invention can be administered to animals prior to infestation in order to prevent infestation (i.e., as a preventative vaccine) and/or can be administered to animals after infestation in order to reduce ectoparasite burden or reduce inflammation (i.e., as a therapeutic vaccine).

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from ectoparasite infestation when administered one or more times over a suitable time period. For example, a preferred single dose of a HRF vaccine or a mimetope thereof ranges from about 1 microgram ($\mu$g, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from ectoparasite infestation. A preferred administration schedule is one in which from about 10 $\mu$g to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-HRF antibody composition ranges from about 1 $\mu$g to about 10 mg of the composition per kilogram body weight of the animal. Anti-HRF antibodies can be re-administered from about 1 hour to about biweekly for several weeks following the original administration. Booster treatments preferably are administered when the titer of antibodies of the animal becomes insufficient to protect the animal from ectoparasite infestation. A preferred administration schedule is one in which from about 10 $\mu$g to about 1 mg of an anti-HRF antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. A naked nucleic acid reagent of the present invention can comprise one or more nucleic acid molecule of the present invention in the form of, for example, a dicistronic recombinant molecule. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccine of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. Naked DNA of the present invention can be contained in an aqueous excipient (e.g., phosphate buffered saline) alone or a carrier (e.g., lipid-based vehicles).

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015/414, filed Feb. 8, 1993, entitled "Recombinant Virus Particle Vaccines", U.S. Pat. No. 5,266,313, by Esposito et al., issued Nov. 30, 1993 and U.S. patent application Ser. No. 08/602,010, by Haanes et al., filed Jan. 15, 1996, entitled "Recombinant Canine Herpesvirus", each of the patents and patent application referred to in this section is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by an ectoparasite as disclosed herein. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, E. coli, Listeria, Mycobacterium, S. frugiperda, yeast, (including Saccharomyces cerevisiae), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

The efficacy of a therapeutic composition of the present invention to reduce ectoparasite infestation of an animal and their surrounding environments can be tested in a variety of ways including, but not limited to, determining (a) reduced the viability of ectoparasites that feed from the treated animal, (b) reduced fecundity of female ectoparasites that feed from the treated animal, (c) reduced reproductive capacity of male ectoparasites that feed from the treated animal, (d) reduced viability of eggs laid by female ectoparasites that feed from the treated animal, (e) altered blood feeding behavior of ectoparasites that feed from the treated animal (e.g., ectoparasites take up less volume per feeding or feed less frequently), (f) reduced viability of ectoparasite larvae, for example due to the feeding of larvae from feces of fleas that feed from the treated animal and/or (g) altered development of ectoparasite larvae (e.g., by decreasing feeding behavior, inhibiting growth, inhibiting (e.g., slowing or blocking) molting, and/or otherwise inhibiting maturation to adults).

One preferred embodiment of the present invention is the use of ectoparasite HRF proteins, nucleic acid molecules, antibodies and inhibitory compounds of the present invention, to protect an animal from flea infestation. Therapeutic compositions are administered to animals in a manner effective to protect the animals from flea infestation. Additional protection may be obtained by administering additional protective compounds, including other flea proteins, nucleic acid molecules, antibodies and inhibitory compounds.

One therapeutic composition of the present invention includes an inhibitor of ectoparasite HRF activity, i.e., a compound capable of substantially interfering with the function of an ectoparasite HRF protein susceptible to inhibition by an inhibitor of ectoparasite HRF activity. An inhibitor of HRF activity can be identified using ectoparasite HRF proteins of the present invention. one embodiment of the present invention is a method to identify a compound capable of inhibiting HRF activity of an ectoparasite. Such a method includes the steps of (a) contacting (e.g., combining, mixing) an isolated ectoparasite HRF protein with a putative inhibitory compound under conditions in which, in the absence of the compound, the protein has HRF activity, and (b) determining if the putative inhibitory compound inhibits the HRF activity. Putative inhibitory compounds to screen include small organic molecules, antibodies (including mimetopes thereof) and analogs. Methods to determine HRF activity are known to those skilled in the art; see, for example, citations in background section and references included therein.

The present invention also includes a test kit to identify a compound capable of inhibiting HRF activity of an ectoparasite. Such a test kit includes an isolated ectoparasite HRF protein having HRF activity and a means for determining the extent of inhibition of HRF activity in the presence of (i.e., effected by) a putative inhibitory compound. Such compounds are also screened to identify those that are substantially not toxic in host animals.

HRF inhibitors isolated by such a method, and/or test kit, can be used to inhibit any HRF that is susceptible to such an inhibitor. Preferred HRF enzymes to inhibit are those produced by ectoparasites. A particularly preferred HRF inhibitor of the present invention is capable of, in an animal, reducing inflammation caused by an ectoparasite. It is also within the scope of the present invention to use inhibitors of the present invention to target HRF-related disorders in animals. Therapeutic compositions comprising HRF inhibitory compounds of the present invention can be administered to animals in an effective manner to protect animals from disease caused by the targeted HRF enzymes. Effective amounts and dosing regimens can be determined using techniques known to those skilled in the art.

One embodiment of the present invention is a method to identify a receptor capable of binding to an isolated HRF protein of the present invention. Such method includes the steps of (a) contacting an isolated ectoparasite HRF protein with a putative receptor compound under conditions in which the HRF protein binds to an HRF receptor obtained by a method comprising: (1) combining a flea HRF protein with a sample having an HRF receptor to form an HRF protein-:HRF receptor complex; and (2) isolating the HRF receptor portion of the HRF protein:HRF receptor complex. Preferably, the sample comprises a cell lysate, in which the cell including a mast cell or a basophil. In particular, the step of isolating comprises: (1) immunoreacting the HRF protein:HRF receptor complex with a ligand capable of selectively binding to the HRF protein to form an immune complex; (2) recovering the immune complex; and (3) purifying the recovered HRF protein from the recovered immune complex.

Another method to identify an HRF receptor, includes the steps of: (a) contacting an isolated flea HRF protein with a putative HRF receptor; and (b) determining if the putative HRF receptor binds to the HRF protein. Preferably, the putative HRF receptor is a protein isolated from a cell including a mast cell or a basophil.

The following examples are provided for the purposes of illustration and are not intended to limit the scope of the present invention.

EXAMPLES

Example 1

This example describes the cloning and sequencing of a HRF nucleic acid molecule.

A flea HRF nucleic acid molecule, denoted nfHRF$_{693}$, was isolated from a bovine-fed flea midgut cDNA library that was immunoscreened with antiserum collected from a rabbit that was immunized with whole flea salivary gland products (as described in PCT Publication No. WO 96/11271, ibid.). Immunoscreening was performed as follows. New Zealand White rabbit antiserum developed against whole flea saliva products was used in the immunoscreening protocols described in the picoBlue™ Immunoscreening Kit instruction manual, available from Stratagene, Inc., La Jolla, Calif. The methods for preparation of the cDNA expression libraries for immunoscreening, i.e., expression of the cDNA clones and procedures for transferring lambda phage plaques to membranes for immunoscreening, are described in the ZAP-cDNA Synthesis Kit instruction manual, also available from Stratagene, Inc.

A nucleotide sequence for the coding strand of the flea HRF nucleic acid molecule named nfHRF$_{693}$ is denoted as SEQ ID NO:1. Translation of SEQ ID NO:1 suggests that nucleic acid molecule nfHRF$_{693}$ encodes a non-full-length flea HRF protein of about 167 amino acids, referred to herein as PfHRF$_{167}$, represented by SEQ ID NO:2, assuming the first codon spans from about nucleotide 1 through about nucleotide 3 of SEQ ID NO:1 and a stop codon spans from about nucleotide 502 through about nucleotide 504 of SEQ ID NO:1. The coding region encoding PfHRF$_{167}$, is represented by nucleic acid molecule nfHRF$_{501}$, having the nucleic acid sequence represented by SEQ ID NO:4 (the coding strand) and SEQ ID NO:5 (the complementary strand). The deduced amino acid sequence SEQ ID NO:2 suggests a protein having a molecular weight of about 19,307.42 kilodaltons (kD) and an estimated pI of about 4.41. A Genbank homology search revealed most homology between SEQ ID NO:4 and a human HRF gene, there being about 53% identity between corresponding regions of both nucleic acid molecules.

---

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 693 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..501

(xi) SEQUENCE DESCRIPTION: SEQ ID NO:1:

```
GAC ATC ATT ACT GGT GAT GAG ATG TTC TCA GAC ACA TAT AAA ATA AAG      48
Asp Ile Ile Thr Gly Asp Glu Met Phe Ser Asp Thr Tyr Lys Ile Lys
 1               5                  10                  15

TTG GTC GAT GAA GTT TTG TAC GAA GTG ACC GGC AAA TTG GTT TCA AGG      96
Leu Val Asp Glu Val Leu Tyr Glu Val Thr Gly Lys Leu Val Ser Arg
             20                  25                  30

TCT CAA GGG GAT ATC CAA ATT GAA GGT TTC AAC CCA TCT GCT GAA GAG     144
Ser Gln Gly Asp Ile Gln Ile Glu Gly Phe Asn Pro Ser Ala Glu Glu
         35                  40                  45

GCT GAT GAA GGA ACT GAA ACA GCC ACG GAA TCT GGT GTT GAT GTG GTC     192
Ala Asp Glu Gly Thr Glu Thr Ala Thr Glu Ser Gly Val Asp Val Val
     50                  55                  60

TTA AAT CAC CGC CTT TGT GAA ACT TTA GCC TTC TCA GAT AAA AAA TCA     240
Leu Asn His Arg Leu Cys Glu Thr Leu Ala Phe Ser Asp Lys Lys Ser
 65                  70                  75                  80

TAC ACT CTT TAT TTA AAA GAT TAT ATA AAA AAA TTG GTG GCG AAA TTA     288
Tyr Thr Leu Tyr Leu Lys Asp Tyr Ile Lys Lys Leu Val Ala Lys Leu
                 85                  90                  95

GAG GAG AAA TCA CCA GAA CAA GTT GAG GTA TTC AAA ACA AAT ATG AAC     336
Glu Glu Lys Ser Pro Glu Gln Val Glu Val Phe Lys Thr Asn Met Asn
            100                 105                 110

AAA GTG ATG AAA GAA ATA TTA AGC CGT TTT AAA GAA ATG CAA ATG TTC     384
Lys Val Met Lys Glu Ile Leu Ser Arg Phe Lys Glu Met Gln Met Phe
        115                 120                 125

ACT GGT GAA TCA ATG GAT TGG GAT CGC ATG GTT GCT CTT ATG GAA TAT     432
Thr Gly Glu Ser Met Asp Trp Asp Arg Met Val Ala Leu Met Glu Tyr
    130                 135                 140

CGT GAA ATA GAT GGT GAA TCT GTT CCA ATT CTG ATG TTC TTT AAA CAT     480
Arg Glu Ile Asp Gly Glu Ser Val Pro Ile Leu Met Phe Phe Lys His
145                 150                 155                 160

GGT CTA GAA GAA GAG AAA TTT TGAACAATAC AACTATTTTA TTTATGTGAA        531
Gly Leu Glu Glu Glu Lys Phe
                165

ACTCCATCTT AATATTACTG TATTTTTGTA TTTATTTTTA TGAATATTTC TCATTTTAAT   591

GACTTACATT TTGTATATAT TTCAAATATG TTGAGTAGTT GAGTTGAGTA TGATCTGTGA   651

ATAATAAAAT AAAGGTTTCA CAATGTAAAA AAAAAAAAA AA                      693

(2) INFORMATION FOR SEQ ID NO:2:

(i) SEQUENCE CHARACTERISTICS:
        (A) LENGTH: 167 amino acids
        (B) TYPE: amino acid
        (D) TOPOLOGY: linear (ii) MOLECULE TYPE: protein (xi) SEQUENCE DESCRIPTION: SEQ ID NO:2:

Asp Ile Ile Thr Gly Asp Glu Met Phe Ser Asp Thr Tyr Lys Ile Lys
 1               5                  10                  15

Leu Val Asp Glu Val Leu Tyr Glu Val Thr Gly Lys Leu Val Ser Arg
             20                  25                  30

Ser Gln Gly Asp Ile Gln Ile Glu Gly Phe Asn Pro Ser Ala Glu Glu
         35                  40                  45

Ala Asp Glu Gly Thr Glu Thr Ala Thr Glu Ser Gly Val Asp Val Val
     50                  55                  60

Leu Asn His Arg Leu Cys Glu Thr Leu Ala Phe Ser Asp Lys Lys Ser
 65                  70                  75                  80

Tyr Thr Leu Tyr Leu Lys Asp Tyr Ile Lys Lys Leu Val Ala Lys Leu
```

```
                        85                  90                  95
Glu Glu Lys Ser Pro Glu Gln Val Glu Val Phe Lys Thr Asn Met Asn
                100                 105                 110
Lys Val Met Lys Glu Ile Leu Ser Arg Phe Lys Glu Met Gln Met Phe
            115                 120                 125
Thr Gly Glu Ser Met Asp Trp Asp Arg Met Val Ala Leu Met Glu Tyr
        130                 135                 140
Arg Glu Ile Asp Gly Glu Ser Val Pro Ile Leu Met Phe Phe Lys His
145                 150                 155                 160
Gly Leu Glu Glu Glu Lys Phe
                165

(2) INFORMATION FOR SEQ ID NO:3:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TTTTTTTTTT TTTTTTACAT TGTGAAACCT TTATTTTATT ATTCACAGAT CATACTCAAC      60

TCAACTACTC AACATATTTG AAATATATAC AAAATGTAAG TCATTAAAAT GAGAAATATT     120

CATAAAAATA AATACAAAAA TACAGTAATA TTAAGATGGA GTTTCACATA AATAAAATAG     180

TTGTATTGTT CAAAATTTCT CTTCTTCTAG ACCATGTTTA AAGAACATCA GAATTGGAAC     240

AGATTCACCA TCTATTTCAC GATATTCCAT AAGAGCAACC ATGCGATCCC AATCCATTGA     300

TTCACCAGTG AACATTTGCA TTTCTTTAAA ACGGCTTAAT ATTTCTTTCA TCACTTTGTT     360

CATATTTGTT TTGAATACCT CAACTTGTTC TGGTGATTTC TCCTCTAATT TCGCCACCAA     420

TTTTTTTATA TAATCTTTTA AATAAAGAGT GTATGATTTT TTATCTGAGA AGGCTAAAGT     480

TTCACAAAGG CGGTGATTTA AGACCACATC AACACCAGAT TCCGTGGCTG TTTCAGTTCC     540

TTCATCAGCC TCTTCAGCAG ATGGGTTGAA ACCTTCAATT TGGATATCCC CTTGAGACCT     600

TGAAACCAAT TTGCCGGTCA CTTCGTACAA AACTTCATCG ACCAACTTTA TTTTATATGT     660

GTCTGAGAAC ATCTCATCAC CAGTAATGAT GTC                                  693

(2) INFORMATION FOR SEQ ID NO:4:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GACATCATTA CTGGTGATGA GATGTTCTCA GACACATATA AAATAAAGTT GGTCGATGAA      60

GTTTTGTACG AAGTGACCGG CAAATTGGTT TCAAGGTCTC AAGGGGATAT CCAAATTGAA     120

GGTTTCAACC CATCTGCTGA AGAGGCTGAT GAAGGAACTG AAACAGCCAC GGAATCTGGT     180

GTTGATGTGG TCTTAAATCA CCGCCTTTGT GAAACTTTAG CCTTCTCAGA TAAAAAATCA     240

TACACTCTTT ATTTAAAAGA TTATATAAAA AAATTGGTGG CGAAATTAGA GGAGAAATCA     300

CCAGAACAAG TTGAGGTATT CAAAACAAAT ATGAACAAAG TGATGAAAGA AATATTAAGC     360
```

-continued

```
CGTTTTAAAG AAATGCAAAT GTTCACTGGT GAATCAATGG ATTGGGATCG CATGGTTGCT      420

CTTATGGAAT ATCGTGAAAT AGATGGTGAA TCTGTTCCAA TTCTGATGTT CTTTAAACAT      480

GGTCTAGAAG AAGAGAAATT T                                                501

(2) INFORMATION FOR SEQ ID NO:5:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AAATTTCTCT TCTTCTAGAC CATGTTTAAA GAACATCAGA ATTGGAACAG ATTCACCATC       60

TATTTCACGA TATTCCATAA GAGCAACCAT GCGATCCCAA TCCATTGATT CACCAGTGAA      120

CATTTGCATT TCTTTAAAAC GGCTTAATAT TTCTTTCATC ACTTTGTTCA TATTTGTTTT      180

GAATACCTCA ACTTGTTCTG GTGATTTCTC CTCTAATTTC GCCACCAATT TTTTTATATA      240

ATCTTTTAAA TAAAGAGTGT ATGATTTTTT ATCTGAGAAG GCTAAAGTTT CACAAAGGCG      300

GTGATTTAAG ACCACATCAA CACCAGATTC CGTGGCTGTT TCAGTTCCTT CATCAGCCTC      360

TTCAGCAGAT GGGTTGAAAC CTTCAATTTG GATATCCCCT TGAGACCTTG AAACCAATTT      420

GCCGGTCACT TCGTACAAAA CTTCATCGAC CAACTTTATT TTATATGTGT CTGAGAACAT      480

CTCATCACCA GTAATGATGT C                                                501
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein selected from the group consisting of: (a) a protein comprising amino acid sequence SEQ ID NO:2, and (b) a flea protein comprising a homologue of a protein of (a), wherein said homologue comprises one or more amino acid deletions, substitutions or insertions, wherein said homologue comprises at least one epitope that elicits an immune response against a protein of (a), wherein said homologue has at least a 6 contiguous amino acid portion identical in sequence to a contiguous 6 amino acid portion of SEQ ID NO:2.

2. The protein of claim 1, wherein said protein is encoded by a nucleic acid sequence selected from the group consisting of SEQ ID NO:1, SEQ ID NO:4, and a fragment of either of said nucleic acid sequences, wherein said fragment is at least about 18 nucleotides in length.

3. The protein of claim 1, wherein said protein comprises a flea protein.

4. The protein of claim 1, wherein said protein is encoded by nucleic acid molecule nfHRF$_{501}$ (characterized by a coding strand having SEQ ID NO:4).

5. The protein of claim 1, wherein said protein is selected from the group consisting of a protein comprising amino acid sequence SEQ ID NO:2 and a protein comprising a fragment of SEQ ID NO:2, wherein said fragment is at least about 6 amino acids in length.

6. The protein of claim 1, wherein said protein is produced by a process comprising culturing a recombinant cell transformed with a nucleic acid molecule encoding said protein to produce said protein.

7. A therapeutic composition to reduce ectoparasite burden of an animal, said therapeutic composition comprising a protective compound comprising an isolated protein selected from the group consisting of: (a) a protein comprising amino acid sequence SEQ ID NO:2, and (b) a flea protein comprising a homologue of a protein of (a), wherein said homologue comprises one or more amino acid deletions, substitutions or insertions, wherein said homologue comprises at least one epitope that elicits an immune response against a protein of (a), wherein said homologue has at least a 6 contiguous amino acid portion identical in sequence to a contiguous 6 amino acid portion of SEQ ID NO:2.

8. The composition of claim 7, wherein said composition further comprises a component selected from the group consisting of an excipient, an adjuvant, a carrier, and a mixture thereof.

9. A therapeutic composition to reduce inflammation in an animal, said therapeutic composition comprising a compound selected from the group consisting of: an isolated protein selected from the group consisting of: (a) a protein comprising amino acid sequence SEQ ID NO:2, and (b) a flea protein comprising a homologue of a protein of (a), wherein said homologue comprises one or more amino acid deletions, substitutions or insertions, wherein said homologue comprises at least one epitope that elicits an immune response against a protein of (a), wherein said homologue has at least a 6 contiguous amino acid portion identical in sequence to a contiguous 6 amino acid portion of SEQ ID NO:2.

10. The composition of claim 9, wherein said inflammation is caused by a flea.

11. The composition of claim 9, wherein said composition further comprises a component selected from the group consisting of an excipient, an adjuvant, a carrier, and a mixture thereof.

12. A method to reduce ectoparasite burden of an animal, said method comprising administering to said animal a therapeutic composition comprising a compound selected from the group consisting of (a) a protein comprising amino acid sequence SEQ ID NO:2, and (b) a flea protein comprising a homologue of a protein of (a), wherein said homologue comprises one or more amino acid deletions, substitutions or insertions wherein said homologue comprises at least one epitope that elicits an immune response against a protein of (a), wherein said homologue has at least a 6 contiguous amino acid portion identical in sequence to a contiguous 6 amino acid portion of SEQ ID NO:2.

13. The method of claim 12, wherein said composition further comprises a component selected from the group consisting of an excipient, an adjuvant, a carrier, and a mixture thereof.

14. The method of claim 12, wherein said animal is selected from the group consisting of dogs and cats.

* * * * *